United States Patent [19]

McGuire et al.

[11] Patent Number: 4,636,466
[45] Date of Patent: Jan. 13, 1987

[54] PHENYLALANINE AMMONIA LYASE-PRODUCING MICROBIAL CELLS

[75] Inventors: Jeffrey C. McGuire, Frederick; John P. Montgomery, Clarksburg; Huei-Hsuing Yang, Olney, all of Md.

[73] Assignee: Genex Corporation, Gaithersburg, Md.

[21] Appl. No.: 547,129

[22] Filed: Oct. 31, 1983

[51] Int. Cl.$^4$ .................. C12P 13/22; C12N 15/00; C12N 9/88; C12N 1/16; C12R 1/645
[52] U.S. Cl. .................. 435/108; 435/172.1; 435/232; 435/255; 435/911
[58] Field of Search .................. 435/108, 232, 255

[56] References Cited

U.S. PATENT DOCUMENTS

| | | | |
|---|---|---|---|
| 2,973,304 | 2/1961 | Huang | 195/47 |
| 3,654,079 | 4/1972 | Tanaka et al. | 435/108 |
| 3,660,235 | 5/1972 | Okumura et al. | 195/37 |
| 3,756,916 | 9/1973 | Leavitt | 195/28 |
| 3,759,790 | 9/1973 | Nakayama et al. | 435/108 |
| 3,791,924 | 2/1974 | Ogata et al. | 435/108 |
| 3,909,353 | 9/1975 | Tsuchida et al. | 435/108 |
| 3,917,511 | 11/1975 | Nakayama et al. | 435/108 |
| 3,957,580 | 5/1976 | Nelson | 195/59 |
| 4,375,515 | 3/1983 | Patel et al. | 435/253 |

FOREIGN PATENT DOCUMENTS 52-10071  1/1977  Japan.
1489468  2/1975  United Kingdom .................. 101/8

OTHER PUBLICATIONS

Ogata, et al., "Metabolism of Aromatic Amino Acid in Microorganisms", Oct. 3, 1966, *Agr. Biol. Chem.* vol. 31, No. 2, pp. 200–206, (1967).

Hodgins, "Yeast Phenylalanine Ammonia-lyase", *The Journal of Biological Chemistry*, Issue of May 10, pp. 2977–2985 (1971).

Havir, et al., "L-Phenylalanine Ammonia-lyase. II. Mechanism and Kinetic Properties of the Enzyme from Potato Tubers", *Biochemistry*, vol. 7, May 1968.

*Primary Examiner*—Lionel M. Shapiro
*Attorney, Agent, or Firm*—Saidman, Sterne, Kessler & Goldstein

[57] ABSTRACT

This invention relates to novel microbial strains which produce phenylalanine ammonia-lyase. These novel microbial strains have the ability to grow on minimal essential media which contain, as substantially the sole carbon source, L-tyrosine. Also disclosed are methods for making phenylalanine ammonia-lyase and methods for making phenylalanine.

17 Claims, No Drawings

PHENYLALANINE AMMONIA LYASE-PRODUCING MICROBIAL CELLS

BACKGROUND OF THE INVENTION

The present invention relates to novel phenylalanine ammonia-lyase producing microorganisms and methods for their selection, production, and use. More particularly, the invention concerns microorganisms which produce relatively high levels of the enzyme, phenylalanine ammonia lyase (hereinafter sometimes called PAL), which in turn, is useful for the production of L-phenylalanine.

L-phenylalanine is an essential amino acid in man, and is, therefore, an important ingredient of enteral and parenteral nutritional formulations. In addition, this amino acid is useful as a starting material for the production of other products, such as the artificial sweetener, aspartame. Various microbial processes for the production of phenylalanine are known. For example, U.S. Pat. No. 3,660,235 describes the production of phenylalanine by phenylalanine analogue resistant strains of Brevibacterium, Corynebacterium, Arthrobacter, Bacillus and Candida. The production of this amino acid by tyrosine-requiring mutants of certain strains of Brevibacterium, Corynebacterium, Arthrobacter, and Escherichia are also known. See U.S. Pat. No. 3,654,079 and 3,909,353.

PAL catalyzes the breakdown of L-phenylalanine to trans-cinnamic acid and ammonia. This enzymatic reaction is reversible, and British Pat. No. 1,489,468 discloses a process for the production of L-phenylalanine which involves the PAL-catalyzed reaction of trans-cinnamic acid with ammonium ions to yield L-phenylalanine. This reaction has been found to be a useful procedure for producing L-phenylalanine, and therefore, there is a continuing need to obtain production microorganisms which produce high levels of PAL activity. Such microorganisms can be used directly for the conversion of cinnamic acid and ammonium ions to L-phenylalanine, or the enzyme can be isolated from the cells and used to produce L-phenylalanine in various forms of bioreactors.

The present invention concerns novel microorganisms which overproduce PAL. These microorganisms are obtained by conventional mutation techniques. Since PAL-containing cells can derive energy from the enzymatic conversion of phenylalanine to trans-cinnamic acid and ammonia and the subsequent metabolism of trans-cinnamic acid, a means for selecting PAL-overproducing mutants involves growing such cells on minimal nutritional media containing L-phenylalanine as substantially the sole carbon source. Although this selection technique can be used for identifying PAL-producing mutants, it has been found that the degradation of L-phenylalanine occurs much more rapidly than subsequent degradative reactions, therefore, the technique is not particularly useful for differentiating those mutants which produce high levels of PAL activity from only nominally productive strains.

SUMMARY OF THE INVENTION

In accordance with the present invention, PAL-producing mutants are selected by growing them on a minimal nutritional medium containing, as substantially the sole carbon source, a phenylalanine analogue. Such analogues are chosen on the basis of their ability to act as substrates for PAL, wherein the PAL-catalyzed breakdown of the analogue is the rate-determining step of the overall metabolism of the analogue to simple metabolites with the concomitant release of biologically useful energy. This technique can be used to select PAL-overproducing strains of any PAL-producing microorganisms, and has been particularly useful in obtaining yeast mutants of the genera, Rhodotorula and Rhodosporidium which produce high levels of PAL activity. These cells may be used for the direct conversion of cinnamic acid and ammonium ions to phenylalanine, or alternatively, can be grown up to produce high levels of PAL, which is subsequently employed for the production of L-phenylalanine.

DETAILED DESCRIPTION OF THE INVENTION

The microbial strains of the present invention are obtained by conventional mutation procedures. Such procedures include, for example, exposing a culture of a parent strain to chemical mutation, using a mutagen such as nitrosoguanidine, ethylmethane sulfonate, 5-bromouracil, hydroxylamine, nitrogen and sulfur mustards, and the like. Irradiating the cells with ultraviolet light or ionizing radiation can also be employed. Such techniques are well known, and are described, for example, in "*Basic Bacteriology,*" La Manna and Mallette, Second Edition, the Williams & Williams Company, Baltimore, 1959, on pages 646 to 649.

Chemical or radiation induced mutation typically produces hundreds to thousands of mutant strains. Selecting viable strains that have the desired characteristics is an arduous task, unless a specific selection procedure can be devised. The present invention involves a selection procedure for PAL-producing mutants, wherein the mutants are grown on a minimal nutrient medium containing, as substantially the sole carbon source, a substrate for the PAL enzyme. Those strains which contain PAL can break down the substrate, thus deriving energy and nutrition. As indicated above, L-phenylalanine is a substrate for PAL, but the enzymatic breakdown of L-phenylalanine to cinnamic acid and ammonia occurs very rapidly, and subsequent degradative reactions become rate-determining. Therefore, although phenylalanine-containing media are selective for mutants that contain PAL, they are not particularly selective for PAL-overproducing strains, because the rate of growth of the mutants is not so much dependent upon the PAL content of the cells but upon the general efficiency of the cell in utilizing phenylalanine metabolites. The selection procedures of the present invention involve growing potential PAL-overproducing mutants on minimal media containing, as substantially the sole carbon source, a PAL substrate which breaks down slowly, as compared to subsequent reactions in the metabolic pathway. The enzymatic breakdown thereby becomes the rate-determining step in the overall utilization of the substrate by the cells for nutritional and energy value. Those cells which grow best on such media have the highest levels of PAL activity. Confirmation of the PAL-producing capability of the cells can be achieved by enzyme activity measurements of cells obtained by the procedures described herein.

Various substrates have been employed in these procedures, and generally any substrate which has a lower activity with respect to PAL degradation than phenylalanine can be employed. Examples of such substrates include, but are not limited to L-phenylalanine methyl ester, L-phenylalanine ethyl ester, m-fluoro-D,L-phenylalanine, L-tyrosine, β-2-thienyl-D,L-alanine and p-fluoro-D,L-phenylanine. A particularly preferred substrate is L-tyrosine. The PAL catalyzed metabolism of L-tyrosine proceeds slowly, and is the rate-determining step in the overall utilization of L-tyrosine as a nutrient. Accordingly, cells which will grow on minimal essential media containing L-tyrosine as substantially the sole carbon source have been found to contain relatively high levels of PAL activity.

When the L-tyrosine medium is inoculated with a population of PAL-containing mutants, growth of the cells usually occurs very slowly. Typically, no growth is seen for several days, following which a few colonies appear. Analysis of these colonies for PAL activity has demonstrated that they produce high levels of PAL activity.

Microbial cells that can be obtained by these procedures include bacteria of the genus Streptomyces and yeasts of the genera Rhodotorula, Rhodosporidium, and Sporobolomyces. After producing mutants from wild-type or known PAL-producing strains, the mutant population is innoculated into a minimal essential medium containing a growth-supporting amount of a PAL substrate as described above. The base minimal medium contains essential vitamins, minerals and a source of nitrogen, but does not contain sufficient quantities of a source of carbon to support microbial growth. This base medium is supplemented with the PAL substrate, preferably L-tyrosine, which thus serves as the sole source of carbon. Generally, concentrations of the PAL substrate from about 1 to about 10, preferably from about 3 to about 7 grams per liter of medium are employed.

Minimal essential media are well known, and typically include phosphate, sulfate, chloride, iodide and molybdate salts of potassium, sodium, iron, manganese, and zinc in concentrations of from about 0.05 to about 1.0 grams per liter. In addition, these media advantageously contain vitamins and growth factors, such as biotin, calcium pantothenate, folic acid, inositol, niacin, p-aminobenzoic acid, pyridoxine hydrochloride, riboflavin, and thiamine hdrochloride, amounts ranging from about 0.1 to about 1.0 grams per liter. The composition of the medium is not critical, and may be composed of a variety of synthetic, semi-synthetic or natural ingredients.

The selection media are preferably solid media (e.g., agar media) to facilitate handling and transfer of cells. These media are sterile and are buffered to a physiologically acceptable pH, e.g. from about 5 to about 8, preferably from about 6 to about 7. Innoculated media are incubated at biologically acceptable temperatures, e.g., from about 20° C. to about 50° C., preferably about 30° C.

The procedures described herein have been found particularly useful for obtaining PAL overproducing mutant-strains of the red yeasts, *Rhodotorula rubra* and *Rhodosporidium toruloides*. These mutants produce large colonies on L-tyrosine enriched minimal essential media and have been shown to produce high levels of PAL by enzyme activity measurements.

PAL is an inducible enzyme in most microorganisms, thus requiring substrate for PAL production. In addition, these enzymes are often subject to catabolite repression. Production processes are therefore advantageously designed to maximize induction of PAL synthesis and minimize catabolic repression.

Generally, PAL is produced by cultivating a PAL-producing strain in a nutritional medium containing assimilable sources of carbon and nitrogen and essential vitamins, minerals and other growth factors. Suitable carbon sources can include various refined or crude carbohydrates such as glucose, sucrose, molasses, starches, grains and the like. A preferred carbon source is glucose syrup.

Nitrogen sources include inorganic ammonium salts, such as ammonium phosphates, ammonium sulfate, ammonium acetate, ammonium citrate, ammonium nitrate and the like and organic nitrogeneous substances such as soybean meal, meat infusion, amino acids, corn steep liquor, protein hydrolyzates, peptones, yeast extracts, and the like. A preferred nitrogen source for the process of this invention is yeast extract.

Vitamins, minerals and other growth factors may be supplied by the carbon and nitrogen sources, or may be provided separately. These components can vary with the particular microorganism employed. Typically, trace minerals such as zinc, manganese, iron, cobalt, and calcium can be supplied in growth promoting amounts as inorganic salts. These minerals may, for example, be supplied with process water, e.g. tap water, sea water, etc. Another growth factor typically supplied is DL-methionine. Nutrient media of the type described are well known, and can vary in composition widely.

Because of the inducible nature of the PAL enzyme in most microorganisms, the cells are conveniently grown to a desired cell density in a conventional medium as described above. After the desired cell growth has been achieved, a PAL inducer can be added to stimulate PAL synthesis. L-phenylalanine is a good PAL inducer, and a number of analogues of L-phenylalanine also induce the synthesis of this enzyme. For example L-tyrosine, L-phenylalanine methylester, or m-fluoro-DL-phenylalanine, can be employed for this purpose.

The PAL inducer is added to the cells in a PAL-inducing amount, which generally ranges from about 0.1 to about 1.0 g/g of cells (dry weight). Preferably, the PAL inducer is employed at a concentration from about 0.2 to about 0.5. During this step, PAL-inducing conditions of temperature, pH, and aeration are maintained. These parameters may vary, and are generally maintained within physiologically compatible limits.

If the cells employed are sensitive to catabolic repression of PAL synthesis, then, prior to induction, means should be employed to reduce or eliminate catabolites and their precursors from the medium. This may be accomplished by separating cells from the medium, washing them and suspending them in a catabolite-free medium. Alternatively, the cells can be allowed to grow until the nutrients are substantially exhausted before the PAL induction procedure is initiated.

The cells are advantageously cultivated under PAL-inducing conditions until the PAL activity reaches about 0.5–2.0 units per ml, preferably about 1.5 units per ml. It has generally been observed that under these conditions, the PAL activity increases to a certain point and then begins to diminish. PAL produced by these procedures may be employed to produce L-phenylalanine from t-cinnamic acid and ammonia. These reactants can be added directly to the PAL-containing cells in an aqueous medium, or the cells or enzyme isolated therefrom can be immobilized by known procedures on a solid support that can be reused for so long as the enzyme activity is maintained.

Phenylalanine is produced by this method under phenylalanine-producing conditions. These conditions will vary, depending upon the particular microbial strains employed, whether whole cells or cell-free enzyme preparations are used and whether immobilized systems are employed. In general, t-cinnamic acid and aqueous ammonia (or soluble ammonium salts) are supplied in amounts such that aqueous ammonia or ammonium salts are in excess. Aqueous ammonia and ammonium salts are employed in amounts from about 3 to about 8 moles per liter. The purpose of the high ammonia concentration is to obtain a high rate of conversion of t-cinnamic acid into phenylalanine. The t-cinnamic acid is employed in amounts of from about 5 to about 30 grams per liter. The concentration of t-cinnamic acid in the reactor is maintained within these ranges by periodic additions of t-cinnamic acid. The pH is maintained within the range of 9.5–11, preferably 10.4–10.8. The temperature is generally maintained within the range of 15–35° C.

L-phenylalanine produced by these methods can be recovered by any suitable means. The solubility of this amino acid is relatively low, therefore, often the product will precipitate from the reaction mixture when the pH is adjusted to its isoelectric point (5.5), and can be recovered by filtration or centrifugation. The product can then be further purified, if desired, by recrystallization or column chromatography. A preferred recovery procedure is described in copending application Ser. No. 547,140, filed Oct. 31, 1983, incorporated herein by reference.

This invention is further illustrated by the following examples, which are not intended to be limiting.

EXAMPLE I

This example describes the mutation and selection of yeast cells to obtain overproducers of PAL.

STRAINS. *Rhodotorula rubra* (ATCC 4056) and *Rhodosporidium toruloides* (ATCC 10788; mating-type alpha) were obtained from American Type Culture Collection, Rockville, Md. USA. Strains were maintained on YE agar (see below). Growth in liquid culture was followed by monitoring optical density at 560 nm. An optical density of 1.0 corresponds to about 0.37 g/L dry cell weight. Cultures were incubated at 30° C.

MEDIA. YE medium contained 15 g of yeast extract per liter. Minimal media all contained, per liter, 1 g monobasic potassium phosphate, 0.5 g magnesium sulfate, 0.1 g sodium chloride, 0.1 g calcium chloride, and 0.4 mg each of biotin, calcium pantothenate, folic acid, inositol, niacin, para-aminobenzoic acid, pyridoxine hydrochloride, riboflavin, thiamine hydrochloride, boric acid, potassium iodide, ferric chloride, manganous sulfate, sodium molybdate, and zinc sulfate. In addition to the above, GP medium contained 10 g of glucose and 5 g L-phenylalanine per liter; PA medium contained 5 g each of L-phenylalanine and ammonium sulfate per liter; and TA medium contained 5 g each of L-tyrosine and ammonium sulfate per liter. Solid media contained 20 g of agar per liter, in addition to the above components.

MUTAGENESIS. Cultures were grown in YE medium to an optical density of 1.5 or greater. Cultures were then centrifuged and resuspended in PA medium at an optical density of 2. N-methyl-N'-nitro-N-nitrosoguanidine (NTG) was added to a final concentration of 20–100 μg/ml, and the cultures were incubated with shaking for 30 minutes at 30° C. Cells were washed before being diluted and plated. For ethylmethane sulfonate (EMS) mutagensis, cells were treated as above, but NTG was replaced by EMS, added to a final concentration of 5 mg/ml. Exposure to EMS was for 60 minutes.

PAL ASSAY. PAL was measured by adding a sample of cells (10–100 μl) to 900 μl of a solution of 50 mM Tris buffer (pH 8.8), 25 mM L-phenylalanine, and 0.001% (wt/vol) of cetylpyridinium chloride. This mixture was incubated in a recording spectrophotometer and the appearance of cinnamic acid was followed at 280 nm (molar absorbance = 16,200). When L-tyrosine was used as substrate, optical density was monitored at 315 nm. A molar extinction coefficient of 10,000 was used for coumaric acid. The rate of increase in optical density was measured during a period of linear increase, usually between one and five minutes after addition of cells. A unit of PAL is the amount of enzyme catalyzing the formation of 0.83 μmole of cinnamic acid per minute at 22° C. or 1 μmole per minute at 30° C. Specific activities are expressed as units of PAL per gram of dry cell weight (U/g).

PAL INDUCTION. For PAL induction, strains were inoculated from agar plates into YE medium and incubated at 30° C. with shaking. When the optical density at 560 nm reached 1.5 or higher, the cultures were centrifuged at 6000×g for 10 minutes. The cell pellets were resuspended in PA medium at an optical density of 1.0. The cultures were then incubated at 30° C. with shaking for times indicated in the text. PAL activity and optical density were then measured.

SUBSTRATE TESTING. A number of phenylalanine analogues were tested as substrates for PAL. The activity of each compound as a substrate for PAL was determined by measuring the rate of increase of absorbance at 280 nm or at 315 nm when PAL-containing cells of *R.rubra* ATCC 4056 were incubated with solutions containing 50 mM Tris buffer (pH 8.8), 0.001% (wt/vol) of cetylpyridinium chloride and 2 mM of the compound to be tested. The results of this testing, shown in Table I indicate that a number of phenylalanine analogues are less efficient than L-phenylalanine as PAL substrates, and thus can be employed for screening PAL-overproducing strains in accordance with the present invention. Such compounds include L-phenylalanine methyl ester, L-phenylalanine ethyl ester, m-fluoro-D,L-alanine and p-fluoro-D,L-phenylalanine.

GROWTH OF MUTANTS ON L-TYROSINE MEDIA. Mutants of *R.rubra* and *R.toruloides* prepared as described above were plated on L-tyrosine containing media (TA plates). Rare colonies appeared after five days of incubation on these media. The size of the colonies was comparable to what was seen after two or three days incubation with L-phenylalanine as carbon source. Several colonies of *R.rubra* and *R.toruloides* were picked from the TA plates and streaked on TA agar. When they had grown, single colonies were induced for PAL as described above. PAL assay results showed that many of these isolates produced high levels of PAL. Four such strains have been shown to produce particularly high levels of PAL activity. These strains have been deposited with the U.S. Department of Agriculture, Agricultural Research Culture Collection, Northern Regional Research Center, Peoria, Ill. USA. These strains were given the designations and accession numbers listed below:

| | | |
|---|---|---|
| R. rubra | GX3243 | NRRL Y-15597 |
| R. rubra | GX3242 | NRRL Y-15596 |
| R. toruloides | GX3249 | NRRL Y-15599 |
| R. toruloides | GX3248 | NRRL Y-15598 |

TABLE I

PAL Substrate Activity of Phenylalanine Analogues

| Compound | Substrate Activity Relative to L-Phenylalanine |
|---|---|
| L-phenylalanine | 100 |
| L-phenylalanine methyl ester | 60 |
| L-phenylalanine ethyl ester | 47 |
| m-fluoro-D,L-phenylalanine | 43 |
| L-tyrosine | 31 |
| β-2-thienyl-D,L-alanine | 27 |
| p-fluoro-D,L-phenylalanine | 20 |
| L-2-amino-3-phenyl-1-propanol | 15 |
| β-phenyl-D,L-serine | 10 |
| m-D,L-tyrosine | 8 |
| β-methyl-D,L-phenylalanine | 5 |
| D-tyrosine | <4 |
| N—CBZ-L-phenylalanine* | <4 |
| N—t-BOC-L-phenylalanine** | <4 |
| p-amino-D,L-phenylalanine | <3 |
| o-D,L-tyrosine | <3 |

*CBZ denotes carbobenzyloxy
**BOC denotes N—tert-butoxycarbonyl

We claim:

1. A method for producing phenylalanine ammonia-lyase which comprises cultivating under PAL-producing conditions a PAL-microbial strain in a nutrient medium containing assimilable sources of carbon, nitrogen and essential minerals and growth factors; wherein the PAL-producing microbial strain is a microorganism which has been isolated by mutation followed by selection for the ability to grow on a minimal essential medium containing, as substantially the sole carbon source, L-tyrosine.

2. The method of claim 1, which further comprises, following growth of the cells of the microbial strain, adding to the cells a PAL inducer.

3. The method of claim 2, which further comprises, prior to adding the PAL-inducer, removing or reducing the concentration of catabolites or their precursors in the nutrient medium.

4. The method of claim 1, 2 or 3, wherein the PAL-producing microbials strain is a bacterium of the genus Streptomyces.

5. The method of claim 1, 2 or 3, wherein the PAL-producing microbial strain is a yeast of the genus Rhodotorula, Rhodospopridium, or Sporobolomyces.

6. The method of claim 5, wherein the PAL-producing microbial strain is Rhodotorula rubra or Rhodosporidium toyuloides.

7. The method of claim 6, wherein the PAL-producing microbial strain is R.rubra, having the identifying characteristics of strain GX3243, NRRL Y-15597.

8. The method of claim 6, wherein the PAL-producing microbial strain is R.rubra, having the identifying characteristics of strain GX3242, NRRL Y-15596.

9. The method of claim 6, wherein the PAL-producing microbial strain is R.toruloides, having the identifying characteristics of strain GX3249, NRRL Y-15599.

10. The method of claim 6, wherein the PAL-producing microbial strain is R.toruloides, having the identifying characteristics of strain GX3248, NRRL Y-15598.

11. A method for producing L-phenylalanine which comprises:
 (a) producing phenylalanine ammonia-lyase by cultivating under PAL-producing conditions a PAL-producing microbial strain in a nutrient medium containing assimilable sources of carbon, nitrogen and essential minerals and growth factors; wherein the PAL-producing microbial strain is a microorganism which has been isolated by mutation followed by selection for the ability to grow on a minimal essential medium containing, as substantially the sole carbon source, L-tyrosine;
 (b) contacting the phenylalanine ammonia-lyase with t-cinnamic acid and ammonia under L-phenylalanine-producing conditions to form L-phenylalanine; and
 (c) recovering the L-phenylalanine.

12. The method of claim 11, which further comprises, following growth of the cells of the microbial strain, adding to the cells a PAL inducer.

13. The method of claim 12, which further comprises, prior to adding the PAL-inducer, removing or reducing the concentration of catabolites or their precursors in the nutrient medium.

14. A culture consisting essentially of R.rubra, having the identifying characteristics of strain GX3243, NRRL Y-15597.

15. A culture consisting essentially of R.rubra, having the identifying characteristics of strain GX3242, NRRL Y-15596.

16. A culture consisting essentially of R.toruloides, having the identifying characteristics of strain GX3249, NRRL Y-15599.

17. A culture consisting essentially of R.toruloides, having the identifying characteristics of strain GX3248, NRRL Y-15598.

* * * * *